US006383786B1

(12) United States Patent
Chauhan et al.

(10) Patent No.: US 6,383,786 B1
(45) Date of Patent: May 7, 2002

(54) METHOD FOR PRODUCING α-HYDROXY ACID FROM α-HYDROXY NITRILE USING NITRILASE

(75) Inventors: Sarita Chauhan, Landenberg, PA (US); Robert Dicosimo, Rockland, DE (US); Robert D. Fallon, Elkton, MD (US); John E. Gavagan; Mark S. Payne, both of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/948,535

(22) Filed: Sep. 7, 2001

Related U.S. Application Data

(62) Division of application No. 09/791,929, filed on Feb. 23, 2001.

(51) Int. Cl.[7] .................................................... C12P 7/40
(52) U.S. Cl. ....................... 435/136; 435/128; 435/227; 435/252.1; 435/252.3; 435/252.38
(58) Field of Search .............................. 435/227, 252.1, 435/252.3, 252.33, 128, 136

(56) References Cited

U.S. PATENT DOCUMENTS

| 3,940,316 A | 2/1976 | Commeyras et al. ......... 195/50 |
|---|---|---|
| 5,223,416 A | 6/1993 | Endo et al. .................. 435/128 |
| 5,234,826 A | 8/1993 | Yamagami et al. ......... 435/139 |
| 5,296,373 A | 3/1994 | Endo et al. .................. 435/280 |
| 5,326,702 A | 7/1994 | Endo et al. .................. 435/129 |
| 5,508,181 A | 4/1996 | Hashimoto .................. 435/129 |
| 5,756,306 A | 5/1998 | Yamaguchi et al. ........ 435/141 |
| 5,814,508 A | 9/1998 | Di Cosimo et al. ......... 435/227 |
| 5,858,736 A | 1/1999 | Di Cosimo et al. ......... 435/121 |
| 6,037,155 A * | 3/2000 | Kobayashi et al. ......... 435/128 |

FOREIGN PATENT DOCUMENTS

| JP | 09028390 | 1/1990 |
|---|---|---|

OTHER PUBLICATIONS

Agricultural Biological Chemistry, vol. 46, p 1165(1982).
Chemical Reviews, vol. 42, p 189 (1948).
Tourneix et al., Antonie Van Leeuwenhoek, 1986, 52: 173–182.

* cited by examiner

Primary Examiner—Nashaat T. Nashed
Assistant Examiner—Christian L. Fronda

(57) ABSTRACT

The present invention relates to a method for producing α-hydroxy acids using an enzyme catalyst having nitrilase activity. More specifically, the invention pertains to use of *Acidovorax facilis* 72W (ATCC 55746) nitrilase to hydrolyze glycolonitrile to glycolic acid. Glycolonitrile is reacted in an aqueous mixture with a catalyst having *Acidovorax facilis* 72W nitrilase activity to give glycolic acid selectively, and at high concentration and high yield.

4 Claims, No Drawings

METHOD FOR PRODUCING α-HYDROXY ACID FROM α-HYDROXY NITRILE USING NITRILASE

This application is a divisional of application Ser. No. 09/791,929, filed Feb. 23, 2001, now allowed.

FIELD OF THE INVENTION

This invention relates to a process for the production of α-hydroxy acids using an enzyme catalyst having nitrilase activity. More specifically, the invention pertains to production of glycolic acid from glycolonitrile using a catalyst having *Acidovorax facilis* 72W nitrilase activity.

BACKGROUND OF THE INVENTION

Glycolic acid ($HOCH_2COOH$; CAS Registry Number is 79-14-1) is the simplest member of the α-hydroxy acid family of carboxylic acids. Its unique properties make it ideal for a broad spectrum of consumer and industrial applications, including use in water well rehabilitation, the leather industry, the oil and gas industry, the laundry and textile industry, and as a component in personal care products like skin creams. Glycolic acid also is a principle ingredient for cleaners in a variety of industries (dairy and food processing equipment cleaners, household and institutional cleaners, industrial cleaners [for transportation equipment, masonry, printed circuit boards, stainless steel boiler and process equipment, cooling tower/heat exchangers], and metals processing [for metal pickling, copper brightening, etching, electroplating, electropolishing]). New technology to commercially produce glycolic acid would be eagerly received by industry.

Various methods for preparing α-hydroxy acids are known, using the corresponding α-hydroxy nitrile as the starting material and a microorganism as the catalyst. Examples of α-hydroxy acids produced include: glycolic acid, lactic acid, 2-hydroxyisobutyric acid, 2-hydroxy-2-hydroxyphenyl propionic acid, mandelic acid, 2-hydroxy-3,3-dimethyl-4-butyrolactone, and 4-methylthiobutyric acid. These products are synthesized using microorganisms, such as those belonging to the genera Nocardia, Bacillus, Brevibacterium, Aureobacterium, Pseudomonas, Caseobacter, Alcaligenes, Acinetobacter, Enterobacter, Arthrobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium, Rhodopseudomonas, Rhodococcus, Corynebacterium, Microbacterium, Obsumbacterium and Gordona. (JP-A-4-99495, JP-A-4-99496 and JP-A-4-218385 corresponding to U.S. Pat. No. 5,223,416; JP-A-4-99497 corresponding to U.S. Pat. No. 5,234,826; JP-A-5-95795 corresponding to U.S. Pat. No. 5,296,373; JP-A-5-21987; JP-A-5-192189 corresponding to U.S. Pat. No. 5,326,702; JP-A-6-237789 corresponding to EP-A-0610048; JP-A-6-284899 corresponding to EP-A-0610049; JP-A-7-213296 corresponding to U.S. Pat. No. 5,508,181.)

However, most known methods for preparing α-hydroxy acids from the corresponding α-hydroxy nitrites as mentioned above do not produce and accumulate a product at a sufficiently high concentration to meet commercial needs. This is frequently a result of enzyme inactivation early in the reaction period. U.S. Pat. No. 5,756,306 teaches that "When an α-hydroxy nitrile is enzymatically hydrolyzed or hydrated using nitrilase or nitrile hydratase to produce an α-hydroxy acid or α-hydroxy amide, a problem occurs in that the enzyme is inactivated within a short period of time. It is therefore difficult to obtain the α-hydroxy acid or α-hydroxy amide in high concentration and high yield." (col. 1, lines 49–54). Maintaining the aldehyde concentration (formed by the disassociation of α-hydroxy nitrile to aldehyde and hydrogen cyanide) and/or the α-hydroxy nitrile concentration in the reaction mixture within a specified range is one method to avoid this problem.

U.S. Pat. No. 5,508,181 addresses further difficulties relating to rapid enzyme inactivation. Specifically, U.S. Pat. No. 5,508,181 mentions that α-hydroxy nitrile compounds partially disassociate into the corresponding aldehydes, according to the disassociation equilibrium. These aldehydes inactivate the enzyme within a short period of time by binding to the protein, thus making it difficult to obtain α-hydroxy acid or α-hydroxy amide in a high concentration with high productivity from α-hydroxy nitriles (col. 2, lines 16–29). As a solution to prevent enzyme inactivation due to accumulation of aldehydes, phosphate or hypophosphite ions were added to the reaction mixture. U.S. Pat. No. 5,326,702 is similar to U.S. Pat. No. 5,508,181, except sulfite, disulfite, or dithionite ions are used to sequester aldehyde and prevent enzyme inactivation. However, the concentration of α-hydroxy acid produced and accumulated even by using such additives as described above is not great.

And finally, U.S. Pat. No. 6,037,155 also teaches that low accumulation of α-hydroxy acid products is related to enzyme inactivation within a short time due to the disassociated-aldehyde accumulation. These inventors suggest that enzymatic activity is inhibited in the presence of hydrogen cyanide (*Agricultural Biological Chemistry*, Vol. 46, page 1165 (1982)) generated in the partial disassociation of α-hydroxy nitrile in water together with the corresponding aldehyde or ketone (*Chemical Reviews*, Vol. 42, page 189 (1948)). The inventors solved the problem of aldehyde-induced enzyme inactivation by using microorganisms whose enzyme activity could be improved by adding a cyanide substance to the reaction mixture. The addition of a cyanide substance limited the disassociation of α-hydroxy nitrile to aldehyde and hydrogen cyanide.

With specific respect to the production of glycolic acid, glycolonitrile is known to reversibly disassociate to hydrogen cyanide and formaldehyde, either of which can inactivate enzyme activity. U.S. Pat. No. 3,940,316 describes a process for preparing an organic acid from the corresponding nitrile using a bacteria with "nitrilasic" activity, and lists glycolonitrile as a substrate. In particular, this patent describes the use of Bacillus, Bacteridium, Micrococcus, and Brevibacterium for this purpose. Though described as having nitrilasic activity, Brevibacterium R312 is the only strain used in all of the U.S. Pat. No 3,940,316 examples. Brevibacterium R312 is known to have nitrile hydratase and amidase activities, but no nitrilase activity (Tourneix et al., *Antonie van Leeuwenhoek*, 1986, 52:173–182).

A method for preparing lactic acid, glycolic acid, and 2-hydroxyisobutyric acid by using a microorganism belonging to Corynebacterium spp. is disclosed in Japanese Patent Laid-open No. Sho 61-56086. JP 09028390 discloses a method for manufacturing high-purity glycolic acid from glycolonitrile by the action of Rhodococcus or Gordona hydrolase. Selectivity for glycolic acid is reported as almost 100%, without formation of glycolic acid amide. U.S. Pat. No. 6,037,155 also provides examples of methods for producing α-hydroxy acids from α-hydroxy nitrites, including glycolic acid. This disclosure acknowledges that not all microbial catalysts can produce high concentrations of glycolic acid due to the aforementioned problems and instructs that screening studies must be conducted in order to find industrially advantageous microorganisms. U.S. Pat. No. 6,037,155 specifically identifies microorganisms belonging to Variovorax spp. and Arthrobacter spp., which are resistant to the suppressing effect of α-hydroxy nitrite or α-hydroxy acid, have durable activity, and can produce the desired product at high concentration.

Acidovorax facilis 72W (ATCC 55746) is characterized by aliphatic nitrilase (EC 3.5.5.7) activity, as well as a combination of nitrile hydratase (EC 4.2.1.84) and amidase (EC 3.5.1.4) activities. U.S. Pat. No. 5,858,736 describes the use of the nitrilase activity of this microbe as a catalyst for the hydrolysis of aliphatic α,ω-dinitriles to the corresponding ω-cyanocarboxylic acids and ammonia in an aqueous reaction mixture. The nitrilase was found to be highly regioselective, where hydrolysis of an α-alkyl-α,ω-dinitrile produced only the ω-cyanocarboxylic acid resulting from hydrolysis of the ω-nitrile group. U.S. Pat. No. 5,814,508 discloses heating a suspension of Acidovorax facilis 72W (ATCC 55746) in a suitable buffer at 35–70° C. for a short period of time to deactivate the undesirable nitrile hydratase and amidase activities of the whole-cell catalyst, without producing a significant decrease in the desired nitrilase activity.

As illustrated above, developing an industrial process using a nitrilase catalyst to efficiently manufacture α-hydroxy acids has proved difficult. When concentration of a product is low, it is well known to those skilled in the art that the process tends to be complex, particularly for separating product from unreacted starting material, or for isolating a small amount of the desired product from a large volume of product mixture. The problem to be solved remains the lack of a facile enzymatic catalyst to convert α-hydroxy nitrites to the corresponding acid in a process characterized by high yield, high concentration and high selectivity, and with the added advantages of low temperature requirements and low waste production.

SUMMARY OF THE INVENTION

The invention provides a process for preparing glycolic acid from glycolonitrile with high specificity at 100% conversion. The invention has the steps of (a) contacting glycolonitrile in a suitable aqueous reaction mixture with an enzyme catalyst characterized by a nitrilase activity derived from Acidovorax facilis 72W (ATCC 55746); and (b) isolating the glycolic acid produced in (a).

Further embodiments of the invention use an enzyme catalyst having nitrilase activity in the form of whole microbial cells, permeabilized microbial cells, one or more cell components of a microbial cell extract, and partially purified enzyme(s), or purified enzyme(s). Microorganisms characterized by a nitrilase activity and useful in the process are Acidovorax facilis 72W (ATCC 55746) and its mutants, Acidovorax facilis 72-PF-15 (ATCC 55747), and Acidovorax facilis 72-PF-17 (ATCC 55745). Additionally, transformed microbial cells containing A. facilis nitrilase activity are included in this invention. Escherichia coli SS1001 (ATCC PTA-1177) and Escherichia coli SW91 (ATCC PTA-1175) are examples of such a transformed microbial cell catalyst.

A further embodiment of the invention uses whole microbial cells characterized by (1) nitrilase activity and (2) nitrile hydratase and amidase activities, as the enzyme catalyst for converting glycolonitrile to glycolic acid. A preferred whole cell is the A. facilis 72W strain. In this embodiment, before use as an enzyme catalyst, the A. facilis 72W whole microbial cells are heated to a temperature of about 35° C. to 70° C. for between 10 and 120 minutes, whereby the nitrile hydratase and amidase activities are destroyed and the nitrilase activity is preserved. This treatment avoids the formation of an unwanted byproduct, glycolamide. Where the mutants and transformed whole microbial cells lack the nitrile hydratase and amidase activities, no heat-treatment step is needed. Escherichia coli SS1001 (ATCC PTA-1177) and Escherichia coli SW91 (ATCC PTA-1175) are examples of a transformed microbial cell catalyst that lacks nitrile hydratase and amidase activities.

In any form and optionally, the enzyme catalyst may be immobilized in or on a soluble or insoluble support.

BRIEF DESCRIPTION OF THE BIOLOGICAL DEPOSITS

Applicants have made the following biological deposits under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| Acidovorax facilis 72-PF-17 | ATCC 55745 | Mar. 8, 1996 |
| Acidovorax facilis 72W | ATCC 55746 | Mar. 8, 1996 |
| Acidovorax facilis 72-PF-15 | ATCC 55747 | Mar. 8, 1996 |
| Escherichia coli SS1001 | ATCC PTA-1177 | Jan. 11, 2000 |
| Escherichia coli SW91 | ATCC PTA-1175 | Jan. 11, 2000 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Applicants have solved the stated problem by providing a process to prepare glycolic acid from the corresponding glycolonitrile in high yields and at high concentration using the nitrilase activity of Acidovorax facilis 72W. A nitrilase enzyme directly converts an aliphatic nitrile to the corresponding carboxylic acid, without forming the corresponding amide as intermediate (Equation 1).

Equation 1

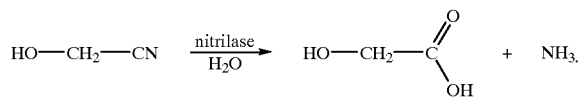

The glycolic acid produced by the present invention has useful applications in a variety of industries.

Definitions:

In this disclosure, a number of terms and abbreviations are used. The following definitions apply unless specifically stated otherwise.

"Enzyme catalyst" or "whole microbial cell catalyst" refers to a catalyst that is characterized by a nitrilase activity. The enzyme catalyst may be in the form of a whole microbial cell, permeabilized microbial cell(s), one or more cell components of a microbial cell extract, partially purified enzyme(s), or purified enzyme(s).

The terms "*Acidovorax facilis*" and "*A. facilis*" are used interchangeably.

The terms "*Escherichia coli*" and "*E. coli*" are used interchangeably.

The term "glycolonitrile" is synonymous with hydroxyacetonitrile, 2-hydroxyacetonitrile, hydroxymethylnitrile, and all other synonyms of CAS Registry Number 107-16-4.

The term "glycolic acid" is synonymous with hydroxyacetic acid, hydroxyethanoic acid, and all other synonyms of CAS Registry Number 79-14-1.

The term "suitable aqueous reaction mixture" refers to the materials and water in which the glycolonitrile and enzyme catalyst come into contact. Tables describing components of the suitable aqueous reaction mixture are provided herein and those skilled in the art appreciate the range of component variations suitable for this process.

The abbreviations in the specification correspond to units of measure, techniques, properties, or compounds as follows: "sec" means second(s), "min" means minute(s), "h" means hour(s), "d" means day(s), "mL" means milliliters, "L" means liters, "mM" means millimolar, "M" means molar, "mmol" means millimole(s), and "wt" means weight. "HPLC" means high performance liquid chromatography, "ca" means approximately, "O.D." means optical density at the designated wavelength, "IU" means International Units.

DESCRIPTION OF THE PREFERRED EMBODIMENTS

Methods and Materials:

Growth of *Acidovorax facilis* Strain 72W (ATCC 55746)

One frozen seed lot vial of *Acidovorax facilis* strain 72W (ATCC 55746) was thawed and the 1 mL contents placed in 500 mL of sterile Inoculum Medium (components listed below in Tables 1 and 2). The inoculum was grown at 30° C. with shaking at 250 rpm in a 2 L flask for 24–30 h.

TABLE 1

Inoculum Medium

| Component | Final Concentration | Component | Final Concentration |
|---|---|---|---|
| potassium phosphate, monobasic | 1.5 g/L | potassium phosphate, dibasic | 3.4 g/L |
| ammonium sulfate | 1.5 g/L | Trisodium citrate, dihydrate | 1 g/L |
| magnesium sulfate, heptahydrate | 0.4 g/L | Trace metal solution (below) | 1 mL/L |
| Amberex 695 (Universal Foods) | 1 g/L | glycerol (sterilized separately) | 8 g/L |

TABLE 2

Trace Metal Solution

| Component | Stock Concentration | Component | Stock Concentration |
|---|---|---|---|
| hydrochloric acid | 10 mL/L | zinc sulfate, heptahydrate | 1.77 g/L |
| calcium chloride, dihydrate | 11.4 g/L | sodium molybdate, dihydrate | 0.05 g/L |

TABLE 2-continued

Trace Metal Solution

| Component | Stock Concentration | Component | Stock Concentration |
|---|---|---|---|
| manganese sulfate, monohydrate | 1.23 g/L | vanadyl sulfate, dihydrate | 0.08 g/L |
| copper sulfate, pentahydrate | 0.63 g/L | nickel nitrate, hexahydrate | 0.04 g/L |
| cobalt chloride, hexahydrate | 0.16 g/L | sodium selenite | 0.04 g/L |
| boric acid | 0.91 g/L | ferrous sulfate, heptahydrate | 6.0 g/L |

The inoculum from the shake flask was transferred aseptically to a presterilized Braun Biostat C fermenter containing Fermenter Medium (components listed below in Table 3). Growth occurred under the following conditions: 32° C., pH 6.8–7.0, dissolved oxygen at 25% of saturation. At inoculation, the fermenter contained 8.5 L of Fermenter Medium plus 218 g of Nutrient Feed solution, giving a starting concentration of approximately 7 g/L glycerol. The Nutrient Feed solution includes the following components that were sterilized separately and combined after cooling: potassium phosphate, monobasic, 19.6 g in 0.25 L deionized water; magnesium sulfate, heptahydrate, 3.3 g, plus sulfuric acid, 4 mL, in 0.15 L deionized water; Trace Metal solution (components listed above in Table 2), 67 mL, plus 400 g glycerol in 0.80 liters deionized water. At 18 h post inoculation, feeding of Nutrient Feed solution began. Initially, the Nutrient Feed solution was added at a rate of 0.4 g feed/min (0.15 g glycerol/min). The culture OD 550 was approximately 8–9. At 26 h, the feed rate was increased to 0.9 g feed/min (0.3 g glycerol/min). The OD 550 was approximately 16–18. A final increase in feed rate to 1.8 g feed/min (0.6 g glycerol/min) was made at 34 h. This rate continued to the end of the run (about 42 h). The final OD 550 was approximately 65–75.

TABLE 3

Fermenter Medium

| Component | Stock Concentration | Component | Stock Concentration |
|---|---|---|---|
| potassium phosphate, monobasic | 0.39 g/L | potassium phosphate, dibasic | 0.39 g/L |
| Difco yeast extract | 5.0 g/L | | |

Cells, as wet cell paste, were recovered by centrifugation and stored frozen until use. Dry cell weight of wet cell paste, obtained by lyophilization, was typically 24% of wet cell weight. For use as a biocatalyst, *A. facilis* 72W (ATCC 55746) cells were first optionally heated to 50° C. for 1 h in 0.35 M phosphate buffer (pH 7.0) to inactivate nitrile hydratase activity.

Use of Nitrilase Activity of *Acidovorax facilis* 72W for Glycolic Acid Production

*A. facilis* 72W whole cells contain a nitrile hydratase and an amidase in addition to the nitrilase. The nitrile hydratase produces glycolamide, an unwanted byproduct leading to yield loss (Example 2). To avoid this byproduct, the *A. facilis* 72W whole cell catalyst can be heat-treated to remove the nitrile hydratase/amidase activities to produce a microbial catalyst which gives high selectivity to glycolic acid with no glycolamide production at concentrations up to 1.0

M glycolic acid (Example 1). Enzymatic activity is sustained in a stable state for a prolonged period of time.

Whole microbial cells can be used as catalyst without any pretreatment such as permeabilization. Alternatively, the whole cells may be permeabilized by methods familiar to those skilled in the art (e.g., treatment with toluene, detergents, or freeze thawing) to improve the rate of diffusion of materials into and out of the cells.

The enzyme catalyst can be immobilized in a polymer matrix (e.g., alginate, carrageenan, polyvinyl alcohol, or polyacrylamide gel (PAG)) or on a soluble or insoluble support (e.g., celite) to facilitate recovery and reuse of the catalyst. Methods for the immobilization of cells in a polymer matrix or on a soluble or insoluble support have been widely reported and are well known to those skilled in the art. The nitrilase enzyme can also be isolated from the whole cells and used directly as catalyst, or the nitrilase can be immobilized in a polymer matrix or on a soluble or insoluble support. These methods have also been widely reported and are well known to those skilled in the art (Methods in Biotechnology, Vol. 1: Immobilization of Enzymes and Cells; Gordon F. Bickerstaff, Editor; Humana Press, Totowa, N.J., USA; 1997).

The concentration of enzyme catalyst in the reaction mixture depends on the specific catalytic activity of the enzyme catalyst and is chosen to obtain the desired rate of reaction. The wet cell weight of the whole microbial cell catalyst in hydrolysis reactions typically ranges from 0.001 g to 0.100 g of wet cells per mL of total reaction volume, preferably from 0.002 g to 0.050 g of wet cells per mL. The specific activity of the whole microbial cell catalyst (IU/gram wet cell wt.) is determined by measuring the rate of conversion of a 0.10 M solution glycolonitrile to glycolic acid at 25° C., using a known weight of whole microbial cell catalyst. An IU of enzyme activity is defined as the amount of enzyme activity required to convert one micromole of substrate to product per minute.

The temperature of the hydrolysis reaction is chosen to optimize both the reaction rate and the stability of the enzyme catalyst activity. The temperature of the reaction may range from just above the freezing point of the suspension (ca. 0° C.) to 70° C., with a preferred range of reaction temperature of from 5° C. to 35° C. The whole microbial cell catalyst suspension may be prepared by suspending the cells in distilled water, or in an aqueous reaction mixture containing a buffer (e.g., sodium or potassium phosphate), where the initial pH of the reaction is between 5.0 and 10.0, and preferably between 6.0 and 8.0. As the reaction proceeds, the pH of the reaction mixture may change due to the formation of an ammonium salt of the α-hydroxy acid from the corresponding nitrile functionality of the α-hydroxy nitrite. The reaction can be run to complete conversion of α-hydroxy nitrile with no pH control, or a suitable acid or base can be added over the course of the reaction to maintain the desired pH.

The glycolic acid thus obtained may be isolated by treating the reaction mixture, from which insoluble matter including the cells has been removed, by procedures well known to those of ordinary skill. Such procedures include but are not limited to concentration, ion exchange, electrodialysis, extraction, and crystallization. The product may be isolated as the ammonium salt, or after acidification, as glycolic acid.

Two mutants of the *Acidovorax facilis* 72W (ATCC 55746) strain have been prepared (U.S. Pat. No. 5,858,736) that produce only very low levels of the undesirable nitrile hydratase activity responsible for non-regioselective nitrile hydrolysis of aliphatic dinitriles. These mutant strains, *Acidovorax facilis* 72-PF-15 (ATCC 55747) and *Acidovorax facilis* 72-PF-17 (ATCC 55745), do not require heat-treatment of the cells before use as an enzyme catalyst to hydrolyze an aliphatic cyanocarboxylic acid ester to the corresponding dicarboxylic acid mono ester.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

In the following examples, the conversion of glycolonitrile to the reaction products glycolic acid and glycolamide was determined by HPLC using a Bio-Rad HPX-87H organic acid analysis column (30 cm×7.8 mm dia.) with precolumn at 50° C. and 0.010 N $H_2SO_4$ as eluent, and a refractive index detector.

Example 1

Conversion of Glycolonitrile to Glycolic Acid Using Nitrilase Activity of *Acidovorax facilis* 72W A suspension of 0.62 g (wet cell paste) *Acidovorax facilis* 72W cells (ATCC 55746) in 9.38 mL of 0.100 M potassium phosphate buffer (pH 7.0) was placed into a 15-mL polypropylene centrifuge tube, and the cell suspension heated at 50° C. for 1 h (to completely inactivate undesired nitrile hydratase and amidase activities), then cooled to 25° C. in a water bath. The suspension was centrifuged and the supernatant decanted: the cell pellet was resuspended in 9.48 mL of 0.020 M potassium phosphate buffer (pH 6.0), mixed at 25° C. for 15 min, and the suspension then centrifuged. The supernatant was decanted. The resulting cell pellet was resuspended in 9.38 mL of 0.020 M potassium phosphate buffer (pH 6.0). To the tube was then added 0.106 mL of a 55 wt % solution of glycolonitrile in water (0.10 M final concentration of glycolonitrile in the suspension), and the resulting suspension mixed on a rotating platform at 25° C. Samples for analysis (0.200 mL) were first adjusted to pH 2.5 with 6 N HCl to stop the reaction, centrifuged, and the supernatant filtered using a 0.2 micron filter. The resulting filtrate was analyzed by HPLC for glycolonitrile, glycolic acid, and glycolamide. After 2 h, the glycolonitrile had been completely converted to glycolic acid and no glycolamide was produced.

An additional 0.312 mL of a 55 wt % solution of glycolonitrile in water (0.30 M additional concentration of glycolonitrile added to the reaction mixture, 0.40 M total) was added to the reaction mixture after complete conversion of the initial concentration of glycolonitrile, and the reaction continued. After 14 h, the additional glycolonitrile was almost completely converted to glycolic acid, and an additional 0.624 mL of a 55 wt % solution of glycolonitrile in water (0.60 M additional concentration of glycolonitrile, 1.0 M total) was added to the reaction mixture. After 40 h, complete conversion of 1.0 M glycolonitrile to glycolic acid was observed, with no production of glycolamide.

Example 2 (Comparative)

Conversion of Glycolonitrile to Glycolic Acid and Glycolamide by *Acidovorax facilis* 72W Cells Having Both Nitrilase and Nitrile Hydratase/Amidase Activities The reaction described in Example 1 was repeated, except that the suspension of *A. facilis* 72W cells in phosphate buffer was not heated at 50° C. for 1 h to inactivate the nitrile hydratase and amidase activities of the cells prior to use in the reaction. A suspension of 0.52 g (wet cell paste) *A. facilis* 72W cells (ATCC 55746) in 9.48 mL of 0.020 M potassium phosphate buffer (pH 6.0) containing 0.106 mL of a 55 wt % solution of glycolonitrile in water (0.10 M final concentration of glycolonitrile in the suspension) was mixed at 25° C. After 2 h, the conversion of glycolonitrile was complete, and the yields of glycolic acid and glycolamide were approximately 61% and 39%, respectively.

An additional 0.312 mL of a 55 wt % solution of glycolonitrile in water (0.30 M additional concentration of glycolonitrile added to the reaction mixture, 0.40 M total) was added to the reaction mixture after 2 h of reaction. After 4 h, a significant amount of the additional glycolonitrile remained, and the ratio of concentrations of glycolic acid and glycolamide was ca. 3.4:1. An additional 0.624 mL of a 55 wt % solution of glycolonitrile in water (0.60 M additional concentration of glycolonitrile, 1.0 M total) was added to the reaction mixture. After 22 h, ca. 40% glycolonitrile remained, and the ratio of concentrations of glycolic acid and glycolamide was ca. 9:1.

Example 3

Conversion of Glycolonitrile to Glycolic Acid Using *Acidovorax facilis* Mutants 72-PF-15 (ATCC 55747) or 72-PF-17 (ATCC 55745)

The reaction described in Example 1 is repeated except that the mutant strains *A. facilis* 72-PF-15 or 72-PF-17 are used instead of *A. facilis* 72W. A suspension of 0.50 g (wet cell paste) *A. facilis* 72-PF-15 or 72-PF-17 in 8.44 mL of 0 020 M potassium phosphate buffer (pH 6.0) is placed into a 15-mL polypropylene centrifuge tube. To the tube is then added 1.06 mL of a 55 wt % solution of glycolonitrile in water (1.0 M final concentration of glycolonitrile in the suspension), and the resulting suspension mixed on a rotating platform at 25° C. Samples of the suspension for analysis (0.200 mL) are first adjusted to pH 2.5 with 6 N HCl to stop the reaction, centrifuged, and the supernatant filtered using a 0.2 micron filter. After sufficient time, complete conversion of glycolonitrile to glycolic acid is obtained with no production of byproduct glycolamide.

Example 4

Conversion of Glycolonitrile to Glycolic Acid Using *E. coli* Transformants SS1001 (ATCC PTA-1177) or SW91 (ATCC PTA-1175)

The reaction described in Example 1 is repeated except that the *E. coli* transformant SS1001 or SW91 is used instead of *A. facilis* 72W. A suspension of 0.50 g (wet cell paste) *E. coli* SS1001 or SW91 in 8.44 mL of 0.020 M potassium phosphate buffer (pH 6.0) is placed into a 15-mL polypropylene centrifuge tube. To the tube is then added 1.06 mL of a 55 wt % solution of glycolonitrile in water (1.0 M final concentration of glycolonitrile in the suspension), and the resulting suspension mixed on a rotating platform at 25° C. Samples of the suspension for analysis (0.200 mL) are first adjusted to pH 2.5 with 6 N HCl to stop the reaction, centrifuged, and the supernatant filtered using a 0.2 micron filter. After sufficient time, complete conversion of glycolonitrile to glycolic acid is obtained with no production of byproduct glycolamide.

What is claimed is:

1. A process for producing an α-hydroxy acid from the corresponding α-hydroxy nitrile comprising
   (a) contacting an α-hydroxy nitrile in a suitable aqueous reaction mixture with a catalyst characterized by a nitrilase activity derived from *Acidovorax facilis* 72W (ATCC 55746); and
   (b) isolating the α-hydroxy acid produced in (a) in the form of a salt or acid.

2. The process of claim 1 wherein the catalyst is in the form of whole microbial cells.

3. A host cell transformed to express the nitrilase activity derived from *Acidovorax facilis* 72W (ATCC 55746).

4. A process for producing an α-hydroxy acid from the corresponding α-hydroxy nitrile comprising
   (a) contacting α-hydroxy nitrile in a suitable aqueous reaction mixture with the transformed host cell of claim 3; and
   (b) isolating the α-hydroxy acid produced in (a) in the form of a salt or acid.

* * * * *